| United States Patent [19] | [11] 4,073,799 |
| Kondo et al. | [45] Feb. 14, 1978 |

[54] PROCESS FOR PRODUCING 3-FORMYLCYCLOPENTANONE DERIVATIVES

[75] Inventors: Kiyoshi Kondo, Yamato; Daiei Tunemoto, Sagamihara; Etsuko Hiro, Tokyo, all of Japan

[73] Assignee: (Zaidanhojin) Sagami Chemical Research Center, Tokyo, Japan

[21] Appl. No.: 661,263

[22] Filed: Feb. 25, 1976

[30] Foreign Application Priority Data

Feb. 27, 1975 Japan .................................. 50-23451
Feb. 27, 1975 Japan .................................. 50-23452
Feb. 27, 1975 Japan .................................. 50-23453
Feb. 27, 1975 Japan .................................. 50-23456

[51] Int. Cl.$^2$ ..................... C07C 69/74; C07C 49/40

[52] U.S. Cl. ............................ 260/345.8 P; 260/141; 260/239 AA; 260/345.9 P; 260/448.8 R; 260/586 F; 260/590 C; 560/9; 560/18; 560/56; 560/119

[58] Field of Search .......... 260/468 D, 514 D, 586 F, 260/590 C, 514 K, 468 K

*Primary Examiner*—Robert Gerstl
*Attorney, Agent, or Firm*—Oblon, Fisher, spivak, McClelland & Maier

[57] ABSTRACT

A novel process for producing 3-formylcyclopentanone derivatives which are useful intermediates for syntheses of five-membered ring compounds such as prostaglandins is disclosed. In the process, 3-formylcyclopentanone derivatives are produced starting from $\beta$-dicarbonyl compounds and azides through several-step reactions.

1 Claim, No Drawings

PROCESS FOR PRODUCING 3-FORMYLCYCLOPENTANONE DERIVATIVES

BACKGROUND OF THE INVENTION

1. Field of the Invention

The present invention relates to a novel process for producing 3-formylcyclopentanone derivatives. The 3-formylcyclopentanone derivatives produced by this process of the invention, have a substituent at the 2-position, and also have a formyl group at the 3-position, which can be converted to the other functional groups or substituents.

Due to their characteristic structures, the 3-formylcyclopentanone derivatives are remarkably useful as intermediates for producing physiologically active natural compounds, especially prostaglandins and derivatives thereof.

Other syntheses of prostanglandins from 3-formylcyclopentanone derivatives are known [A. Greene and P. Crabbe; Tetrahedron Lett., 2215 (1975)].

The present invention relates to a novel process for producing both these useful compounds and other novel compositions of matter which are necessary for the process of this invention.

2. Description of the Prior Art

Heretofore, for the purpose of producing prostaglandins and other related compounds, various synthetic methods using the cyclopentanone ring have been disclosed. Typical methods include:

(1) The Dieckmann reaction of alkyl adipate to produce 2-alkoxycarbonylcyclopentanones [P. S. Pinkney, Org. Syntheses, Coll. Vol., 2, 116 (1943)];

(2) The Aldol condensation of 1,4-dicarbonyl compounds to produce substituted cyclopentanones [R. A. Ellison, Synthesis, 397 (1973)] and (3) The Diels Alder reaction of substituted cyclopentadienes followed by oxidation and iodolactonization to produce the basic skelton of prostagrandin. [E. J. Corey, et al., J. Amer. Chem. Soc., 93, 1489 (1971)].

These processes in some ways have certain advantages. However, they are subject to several significant disadvantages: most of them can only be applied to the synthesis of simple systems; the selectivity of the reaction is very low in some cases; expensive or dangerous reagents are required; establishment of easy and operable conditions at some stages of the synthetic reactions is difficult; and purification of the products is difficult. Accordingly, these methods are generally not employed as industrial synthetic methods.

It has also been proposed to use bicyclo[3.1.0]hexane derivatives as intermediates in Processes for Producing Prostaglandins [W. P. Schneider, Chem. Commun. 304 (1969); E. J. Corey, J. Amer. Chem. Soc., 94, 4014 (1972)].

However, the yield obtained for the ring cleavage reaction of the cyclopropane ring is very low and furthermore, the reaction is not stereospecific.

Accordingly, this route is considered to be of less value as a practical method. Among these methods, processes which utilize 3-formylcyclopentanone derivatives as a starting material have been considered to be the most effective and broadly applicable methods for synthesis of natural and modified prostaglandins and derivatives thereof, e.g. prostanoids, which have similar structure and, in some cases have more selective and higher physiological activity than the natural products.

For the synthesis of 3-formylcyclopentanone derivatives, the following four methods have already been disclosed:

(1) the Michael addition of nitromethane to substituted cyclopentenones, followed by the Nef reaction [J. Bagli, et al., Tetrahedron Lett., 3815 (1972)];

(2) the addition of hydrogen cyanide to cyclopentenone derivatives followed by reduction of the nitrile group [M. P. L. Caton, et al., Tetrahedron Lett., 773 (1972)];

(3) The conjugate addition of olefins to substituted cyclopentenones followed by ozonolysis of the olefin. [F. S. Alvarez, et al., J. Amer. Chem. Soc., 94, 7823 (1972)]; and (4) the utilization of the photochemical reaction product of tropolone as a starting material. [P. Crabbe, et al., Tetrahedron Lett., 2215 (1975)].

However, all of these methods have one or more of the following disadvantages: the starting materials are not easily available; the selectivity of the reaction is low; expensive or dangerous reagents are required; and the range of the suitable reaction conditions is narrow and thus reproducibility of the reaction is poor.

Accordingly, these methods cannot be employed in industrial processes.

DESCRIPTION OF THE PREFERRED EMBODIMENTS

Attempts have been made to find novel synthetic methods of producing 2,3-disubstituted cyclopentanone derivatives which are not known in the prior art and also to uncover novel industrial processes for producing 2,3,4-tri-substituted cyclopentanone derivatives. The result of these efforts has been the discovery of a new process which can easily be applied to the preparation of 3-formylcyclopentanone derivatives. The process of this invention can be summarized by the following reaction scheme:

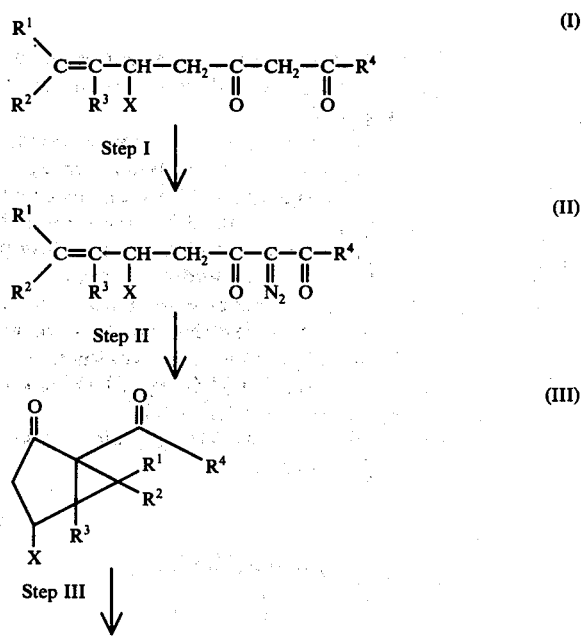

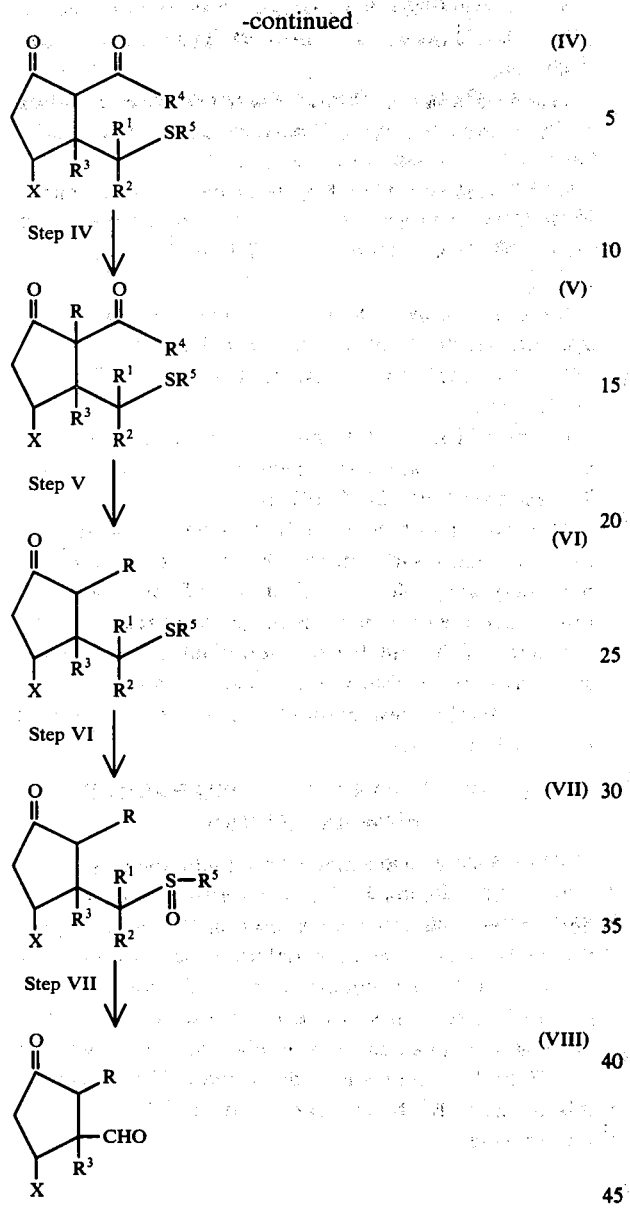

wherein $R^1$, $R^2$ and $R^3$ respectively represent a hydrogen atom or a lower alkyl group; $R^4$ represents an alkyl group or an alkoxy group;

$R^5$ represents a residual hydrocarbon group having less than 10 carbon atoms; X represents a hydrogen atom or an alkoxy, tetrahydropyranyloxy or silyloxy group; and R represents an unsubstituted or substituted alkyl or alkenyl group; provided that in the case of Step VII, $R^1$ and $R^2$ each represents a hydrogen atom.

Each step of the synthetic scheme will be illustrated in more detail. It should be noted that in the following the compounds are described by conventional nomenclature, for example, pentanoic acid ($C_4H_9COOH$) and cyclopentanecarboxylic acid ($C_5H_9COOH$).

In Step I of the reaction, the starting $\beta$-dicarbonyl compounds having the formula

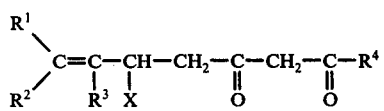
(I)

($R^1$, $R^2$, $R^3$, $R^4$ and X are defined above), can be easily produced by the condensation or addition reaction of acetoacetic acid esters or acetylacetones to the corresponding alkylhalides or carbonyl compounds (as shown in the References Examples).

Suitable compounds having the formula (I) include $\beta$-ketoesters such as 3-oxo-6-heptenoic acid esters; 3-oxo-6-octenoic acid esters; 3-oxo-7-methyl-6-octenoic acid esters, 3-oxo-5-hydroxy-6-heptenoic acid esters, 3-oxo-5-trimethylsiloxy-6-heptenoic acid esters and 3-oxo-6-methyl-6-heptenoic acid esters; and $\beta$-diketones such as 7-octene-2,4-dione, 7-nonene-2,4-dione, 8-methyl-7-nonene-2,4-dione, 7-methyl-7-octene-2,4-dione and 6-alkoxy-7-octene-2,4-dione. Step I comprises reaction of the $\beta$-dicarbonyl compound (I) with an azide.

Suitable azides include tosyl azide, benzenesulfonyl azide, phenyl azide, azidoformic acid esters and other various azides.

The reaction of the Step I should be conducted under basic conditions. Suitable condition can be attained by addition of alkali metal hydroxides, such as sodium hydroxide and potassium hydroxide; alkali metal alkoxides, such as sodium methoxide, sodium ethoxide, sodium t-butoxide, potassium t-butoxide; and organic amines, such as triethylamine, tributylamine, dimethylaniline, pyridine and piperidine to the reaction system. The amount of the base to be added is preferably about an equimolar portion with respect to the starting materials.

In the operation of Step I, the reaction can be conducted without using a solvent. However, in order to increase the yield of the product under mild reaction conditions, it is preferred to use a solvent such as acetonitrile, dimethylformamide, tetrahydrofuran, alcohols, ethers, methylene chloride and the like.

When the operation of Step I is conducted under these conditions, the reaction can be performed smoothly without specific heating or cooling of the system to produce $\alpha$-diazo-$\beta$-dicarbonyl compounds.

Typical $\alpha$-diazo-$\beta$-dicarbonyl compounds having the formula (II)

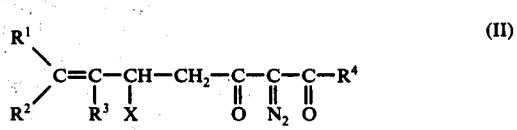
(II)

($R^1$, $R^2$, $R^3$, $R^4$ and X are defined above) produced by Step (I) include $\alpha$-diazo-$\beta$-ketoesters such as 3-oxo-2-diazo-6-heptenoic acid esters, 3-oxo-2-diazo-6-octenoic acid esters, 3-oxo-2-diazo-7-methyl-6-octenoic acid esters, 2-diazo-3-oxo-5-trimethylsiloxy-6-heptenoic acid esters, 2-diazo-3-oxo-5-(2'-tetrahydropyranyloxy)-6-heptenoic acid esters, 5-benzyloxy-2-diazo-3-oxo-6-heptenoic acid esters, 2-diazo-3-oxo-6-methyl-6-heptenoic acid esters; and $\alpha$-diazo-$\beta$-diketones such as 7-octene-3-diazo-2,4-dione, 7-nonene-3-diazo-2,4-dione, 8-methyl-7-nonene-3-diazo-2,4-dione, 7-methyl-7-octene-3-diazo-2,4-dione, 6-alkoxy-7-octene-3-diazo-2,4-dione and the like.

In Step II, it is necessary to subject $\alpha$-diazo-$\beta$-dicarbonyl compounds having the formula (II) to conditions which enable the formation of carbenes or carbenoids.

The carbene or carbenoid forming conditions can be attained by (1) treatment with a catalyst or (2) photoirradiation.

In the catalized decomposition method, a trace amount of catalyst comprising for example metals or metal oxides, e.g., copper powder, copper brone, copper halides, cupper sulfate, copper acetylacetonate, copper-phosphine complex, silver oxide, silver nitrate and the like, is used in an inert atmosphere to form carbenoids.

In the photodecomposition method, compound (II) is directly irradiated or irradiated in an inert atmosphere to form carbenes. Conventional light sources used in the photochemical industries such as a low pressure mercury lamp or a high pressure mercury lamp can be used as the light source.

It is not always necessary to use a solvent in either the catalytic method or the photodecomposing method. However, in order to avoid the formation of by-products, and to obtain the desired compound in high yield and selectivity, it is preferred to conduct the reactions in an inert medium. Suitable inertness can be attained by conducting the reaction under an inert atmosphere, such as nitrogen or argon gas and using a solvent such as benzene, toluene, xylene, hexane, petroleum ether and the like, as the reaction medium.

The carbenes or carbenoids formed under these conditions immediately and selectively result in a cyclo-addition to the unsaturated double bond of the same molecule to produce bicyclo [3.1.0] hexane-2-one derivatives in high yield.

The bicyclo compounds produced by the reaction of Step II reaction, have electron withdrawing substituents at the 1-position.

Accordingly, it makes easier to cleave the cyclopropane ring by the nucleophilic attack of the next step. Moreover, the substituent also controls the direction of ring cleavage. In other words, as a result of having the appropriate substituent at its 1-position, the desired one of the three carbon-carbon bonds of the cyclopropane ring can, be selectively cleaved to produce cyclopentanone derivatives.

Typical bicyclo [3.1.0] hexane-2-one derivatives having the formula (III)

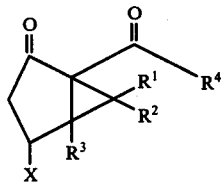
(III)

($R^1$, $R^2$, $R^3$, $R^4$ and X are defined above) which are produced by Step II, include 2-oxo-bicyclo [3.1.0] hexane-1-carboxylic acid esters, 4-hydroxy-2-oxo-bicyclo[3.1.0] hexane-1-carboxylic acid esters, 2-oxo-4-trimethylsiloxy-bicyclo [3.1.0] hexane-1-carboxylic acid esters, 2-oxo-4-(2'-tetrahydropyranyloxy)-bicyclo [3.1.0] hexane-1-carboxylic esters, 4-benzyloxy-2-oxo-bicyclo [3.1.0] hexane-1-carboxylic acid esters, 6-methyl-2-oxo-bicyclo [3.1.0] hexane-1-carboxylic acid esters, 4-hydroxy-6-methyl-2-oxo-bicyclo [3.1.0] hexane-1-carboxylic acid esters, 6-methyl-2-oxo-4-trimethylsiloxy-bicyclo [3.1.0] hexane-1-carboxylic acid esters, 6-methyl-2-oxo-4-(2'-tetrahydropyranyloxy)-bicyclo[3.1.0] hexane-1-carboxylic acid esters, 6,6-dimethyl-2-oxo-bicyclo (3.1.0) hexane-1-carboxylic acid esters, 1-acetyl-bicyclo [3.1.0] hexane-2-one, 1-acetyl-4-hydroxybicyclo [3.1.0] hexane-2-one, 1-acetyl-4-trimethylsiloxy-bicyclo [3.1.0] hexane-2-one, 1-acetyl-4-(2'-tetrahydropyranyloxy)-bicyclo [3.1.0] hexane-2-one and 1-acetyl-6-methyl-bicyclo [3.1.0] hexane-2-one and the like.

In Step III reaction, it is necessary to react the bicyclo [3.1.0] hexane-2-one derivative having the formula (III) with a mercaptan having the formula $R^5SH$ in the presence of a base.

Suitable bases include alkali metal hydroxides such as potassium hydroxide and, sodium hydroxide; alkali metal alkoxides such as sodium methoxide, potassium methoxide, sodium ethoxide and, potassium t-butoxide; and organic amines such as triethyl amine, tributyl amine, pyridine and the like.

Suitable amount of the base range from catalytic to excess amounts. However, it is preferred to use about equimolar amounts of the base and the starting material, in order to shorten the reaction time and to increase the yield.

It is theorized that the base used in Step III, may act in the reaction system as a reagent for forming a mercaptide anion from the mercaptan $R^5SH$.

The attack of the anion on the bicyclo ring results in a partial cleavage of the ring to form an anionic species having the formula (III'), and then the anions (III') are converted to the product (IV).

Accordingly, the process of this invention includes the method of using mercaptide anions which can be produced by the reaction of $R^5SH$ with a wide variety of bases.

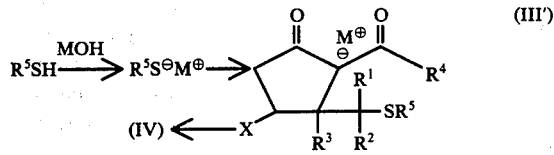
(III')

In the operation of Step III, it is preferred to use a solvent. The solvents are preferably polar solvents which are inert to the reaction, such as alcohols, e.g. methanol, ethanol and, t-butanol; ethers, e.g. diethyl ether and, tetrahydrofuran; dimethylformamide, acetonitrile, dimethyl sulfoxide and the like. It is also possible to effect the process of this invention by using a large excess amount of the mercaptans as a solvent. Under the above-mentioned conditions, the reaction can be conducted smoothly at room temperature without any specific heating or cooling. Suitable cyclopentanone compounds having an electron withdrawing substituent at the 2-position represented by the formula (IV)

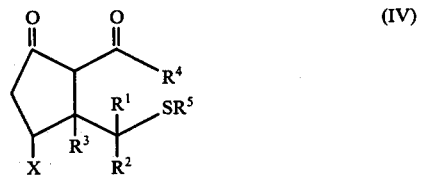
(IV)

($R^1$, $R^2$, $R^3$, $R^5$ and X are defined above) include 2-oxo-5-phenylthiomethyl-cyclopentanecarboxylic acid esters, 5-(1'-phenylthioethyl)-2-oxo-cyclopentanecarboxylic acid esters, 5-benzylthiomethyl-2-oxo-cyclopentanecarboxylic acid esters, 5-hexylthiomethyl-2-oxo-cyclopentanecarboxylic acid esters, 2-oxo-5-phenylthiomethyl-4-trimethylsiloxy-cyclopentanecarboxylic acid esters, 2-oxo-5-phenylthiomethyl-4-(2'-tetrahydropyranyloxy)-cyclopentanecarboxylic acid esters, 4-benzyloxy-2-oxo-5-phenylthiomethyl-cyclopentanecarboxylic acid esters, 5-methyl-2-oxo-5-phenylthiomethyl-cyclopentanecarboxylic acid esters, 5-methoxymethyl-2-oxo-cyclopentanecarboxylic acid esters, 2-oxo-5-(1'-phenylthioethyl)-cyclopentanecarboxylic acid esters, 2-acetyl-3-phenylthiomethyl-cyclopentanone and the like.

These cyclopentanone derivatives having an electron withdrawing substituent at the 2-position and a thiomethyl substituent at the 3-position which are produced by the process of this invention, contain only desirable functions which can be easily transformed into the substituent desired on the prostanoids. The advantage of an electron withdrawing group at the 2-position is its strong and selective activation of the 2-position. Thus it is easy to introduce various kind of alkyl or alkenyl substituent at this position.

Moreover, the activating group can easily be removed after the reaction. The advantage of a thiomethyl substituent at the 3-position is that, although the sulfide linkage itself is rather inert to normal chemical reactions, it can be converted to other effective functional groups e.g., the formyl group, by oxidation followed by a Pummerer rearrangement.

The latter capability enables the introduction of a desired side chain on the prostaglandins.

In the reaction of Step IV, it is necessary to condense the cyclopentanone compounds having the formula (IV) with an alkylating agent having the formula RZ, wherein R represents an unsubstituted or substituted alkyl or alkenyl group and Z represents a halogen atom, a tosyloxy, or an acyloxy group, in the presence of a base.

Suitable alkylating agents having the formula RZ include conventional typical alkylating agents such as alkyl halides, benzyl halides, p-toluenesulfonic acid alkyl esters; and also functionized alkylating agents such as ω-haloheptanoic acid esters, ω-halo-δ-unsaturated heptanoic acid esters. The latter two are necessary units for producing prostaglandins.

Suitable base to be used in the Step IV include alkali metal carbonates such as potassium carbonate and sodium carbonate; alkali metal hydroxides such as potassium hydroxide and, sodium hydroxide; alkali metal alkoxides such as sodium methoxide, potassium methoxide, sodium ethoxide, and potassium t-butoxide; and organic amines such as triethyl amine, tributyl amine, pyridine and the like.

For good performance of the Step IV reaction, it is preferred to use an equimolar or a slightly excessive amount of the base relative to the amount of starting material. In the Step IV reaction, it is also preferred to use a solvent which will not adversely affect the starting materials and products, such as alcohols, e.g., methanol, ethanol and, t-butanol; ethers, e.g., diethyl ether, tetrahydrofuran; benzene, toluene, xylene, dimethylformamide, acetonitrile, and dimethyl sulfoxide.

The reaction can be conducted smoothly at room temperature without special heating or cooling.

Typical cyclopentanone derivatives having the formula (V)

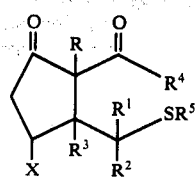

($R^1$, $R^2$, $R^3$, $R^4$, $R^5$ and X are defined above) which are produced in Step IV include 1-methyl-2-oxo-5-phenylthiomethyl-cyclopentanecarboxylic acid esters, 2-oxo-1-phenyl-5-phenylthiomethyl-cyclopentanecarboxylic acid esters, 1-benzyl-2-oxo-5-phenylthiomethyl-cyclopentanecarboxylic acid esters, 4-hydroxy-1-methyl-2-oxo-5-phenylthiomethyl-cyclopentanecarboxylic acid esters, 1-methyl-2-oxo-5-phenylthiomethyl-4-trimethylsiloxy-cyclopentanecarboxylic acid esters, 1-methyl-2-oxo-5-phenylthiomethyl-4-(2'-tetrahydropyranyloxy)-cyclopentanecarboxylic acid esters, 1-ethoxycarbonylmethyl-2-oxo-5-phenylthiomethyl-cyclopentanecarboxylic acid esters, 1-(6'-methoxycarbonyl hexyl)-2-oxo-5-phenylthiomethyl-cyclopentanecarboxylic acid esters, 1,5-dimethyl-2-oxo-5-phenylthiomethyl-cyclopentanecarboxylic acid esters, 1-methyl-2-oxo-5-(1'-phenylthioethyl)-cyclopentanecarboxylic acid esters and the like.

In the reaction of Step V, it is necessary to heat-treat the cyclopentanone derivatives having the formula (V) in the presence of an alkali metal salt. Suitable alkali metal salts include iodides, bromides or cyanides of sodium, potassium or lithium metal, hydrates thereof and the like.

In order to attain the maximum yield of the desired product, it is prefered to use lithium iodide or a hydrate thereof or sodium cyanide. The use of about an equimolar amount of the alkali metal salt relative to the starting material is sufficient for the performance of the reaction.

The heat-treatment of Step V is usually conducted at 50° – 200° C, preferably at 100° – 150° C.

The heat-treating time is dependent upon the type of alkali metal salt used and the reaction temperature, but is usually within the range of from 30 minutes to 3 hours.

In conducting the Step V reaction, it is also preferred to use a solvent, especially polar solvent such as amines, e.g., pyrilidine, piperidine or, collidine; dimethylformamide, acetonitrile, dimethyl sulfoxide, hexamethylphosphoric triamide and the like, all of which are inert to the reaction.

As an alternative method for the Step V reaction, the cyclopentanone derivatives having the formula (V) can first be hydrolyzed and then decarboxylated to produce the desired product, i.e., the cyclopentanone derivatives (VI).

The hydrolysis step is usually conducted in an aqueous medium in the presence of an acid or an alkali.

Suitable acids include mineral acids, e.g., hydrochloric acid, sulfuric acid, perchloric acid, phosphoric acid; and organic acids, e.g., p-toluenesulfonic acid, acetic acid and the like.

Suitable alkali include the common hydrolysis reagents such as sodium hydroxide, potassium hydroxide, sodium carbonate, potassium carbonate and the like.

In the case of acid hydrolysis, a catalytic amount of the acid is sufficient. On the other hand, in the case of base hydrolysis, the use of an equimolar or an excess amount of the alkali is preferred.

The hydrolysis is usually conducted at 0° - 150° C, preferably 50° - 100° C. In the hydrolysis under acidic conditions, the decarboxylation step can also be performed simultaneously by heating the reaction system.

On the other hand, when the compound (V) is hydrolyzed under alkaline conditions, the reaction system must first be neutralized or slightly acidified to a pH of around 4 after the reaction is completed. Then the resulting carboxylic acid should be heat-treated to attain the decarboxylation reaction.

The heat-treating time is dependent upon the nature of the starting materials and the reaction temperature, but is usually within the range of 30 minutes to 3 hours.

In this modification of the Step V reaction, the hydrolysis step should be conducted in an aqueous medium such as water, or preferably in a mixture of water and a water-miscible solvent such as tetrahydrofuran, acetone, acetonitrile, alcohols and the like.

Typical cyclopentanone sulfide derivatives having the formula (VI)

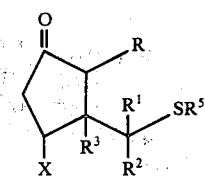

(VI)

($R^1$, $R^2$, $R^3$, $R^5$, R and X are defined above) which are produced in Step V, include 1-methyl-2-phenylthiomethylcyclopentanone, 1-methyl-2-(p-tolylthiomethyl)-cyclopentanone, 3-hydroxy-1-methyl-2-phenylthiomethyl-cyclopentanone, 1-methyl-2-phenylthiomethyl-3-trimethylsiloxy-cyclopentanone, 1-pentyl-2-phenylthiomethyl-cyclopentanone, 1-(2'-pentenyl)-2-phenylthiomethyl-cyclopentanone, 1,2-dimethyl-2-phenylthiomethyl-cyclopentanone, 2-oxo-5-phenylthiomethyl-cyclopentaneheptanoic acid methyl ester, 4-hydroxy-2-oxo-5-phenylthiomethyl-cyclopentaneheptanoic acid methyl ester, 2-oxo-4-(2'-tetrahydropyranyloxy)-5-phenylthiomethyl-cyclopentaneheptanoic acid methyl ester, 5-methyl-2-oxo-5-phenylthiomethyl-cyclopentaneheptanoic acid methyl ester, 2-oxo-5-phenylthiomethyl-cyclopentaneheptanoic acid methyl ester, 1-ethoxycarbonylmethyl-3-phenylthiomethyl-cyclopentanone and the like.

In the Step VI reaction, it is essential to oxidize the cyclopentanone sulfide derivatives having the formula (VI) with an oxidizing agent.

Suitable oxidizing agents include inorganic oxidizing agents such as sodium metaperiodate, hydrogen peroxide, oxygen, ozone, manganese dioxide, selenium dioxide, chromic acid, nitric acid and, dinitrogen tetroxide, and also organic oxidizing agents, such as peracetic acid, perbenzoic acid, m-chloroperbenzoic acid, iodosobenzene and the like.

In order to perform the oxidation without any deleterious effects on the other functional groups such as the carbonyl, hydroxyl, and/or ester groups of the molecule, it is preferred to use organic peracids, especially perbenzoic or m-chloroperbenzoic acid. The necessary amount of the oxidizing agent is usually an equimolar or slightly excessive amount relative to the amount of starting material. The desired sulfoxides can be selectively produced by appropriate selection of the reaction conditions such as the amount of the oxidizing agent, the reaction temperature, and the reaction time.

In the operation of Step VI, it is preferred to use a solvent such as water, an alcohol, e.g., methanol an ethanol; and acetic acid; chloroform, methylene chloride, benzene and the like, all of which are inert in the reaction concerned.

Typical cyclopentanone sulfoxides having the formula (VII)

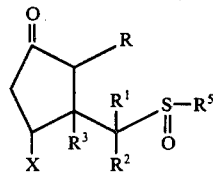

(VII)

($R^1$, $R^2$, $R^3$, $R^5$, X and R are defined above) which are produced by the Step VI reaction include 2-benzenesulfinylmethyl-1-methyl-cyclopentanone, 2-benzenesulfinylmethyl-1-benzyl-cyclopentanone, 2-toluene-sulfinylmethyl-1-methyl-cyclopentanone, 2-benzenesulfinylmethyl-3-hydroxy-1-methyl-cyclopentanone, 2-benzenesulfinylmethyl-1-methyl-3-trimethylsiloxy-cyclopentanone, 2-benzenesulfinylmethyl-1-pentyl-cyclopentanone, 2-benzenesulfinyl-methyl-1-(2'-pentenyl)-cyclopentanone, 2-benzenesulfinylmethyl-1,2-dimethyl-cyclopentanone, 5-benzenesulfinylmethyl-2-oxo-cyclopentaneheptanoic acid methyl ester, 5-benzenesulfinylmethyl-4-hydroxy-2-oxo-cyclopentaneheptanoic acid methyl ester, 5-benzenesulfinylmethyl-2-oxo-4-trimethylsiloxycyclopentaneheptanoic acid methyl ester, 5-benzenesulfinylmethyl-2-oxo-4-(2'-tetrahydropyranyloxy)-cyclopentaneheptanoic acid methyl ester, 5-benzenesulfinylmethyl-5-methyl-2-oxo-cyclopentaneheptanoic acid methyl ester, 5-benzenesulfinylmethyl-2-oxo-cyclopentaneheptanoic acid methyl ester and the like.

The compounds obtained by the reactions of Steps III, IV, V and VI, i.e., compounds IV, V, VI and VII, and also the cyclopentanone sulfones, represented by the formula (IX)

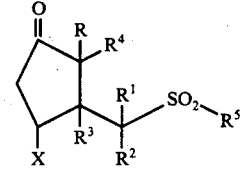

(IX)

wherein $R^1$, $R^2$, $R^3$, $R^5$, R and X are all defined above and wherein $R^4$ represents a hydrogen atom, an acyl or an alkoxycarbonyl group, the sulfones being obtainable by the oxidation of cyclopentanone derivatives IV, V, VI and VII, are structurally quite similar to prostagrandins. Thus, all of these compounds are expected to be physiologically active as a sulfur analogue of prostangrandins.

In the reaction of Step VII, it is necessary to treat the cyclopentanone sulfoxide having the formula (VII) with an organic acid anhydride and then to treat the resultant product with an acid or an alkali.

Suitable organic acid anhydrides for use in the first stage of the Step VII reaction include acetic anhydride, benzoic anhydride and the like.

In the reaction, it is not always necessary to use a solvent. However, it is possible to use a solvent which will not adversely effect the reaction product, such as chloroform, methylene chloride, benzene and the like. If desired, it is also possible to add a buffering agent such as an alkali metal salt, e.g., sodium acetate, to the reaction system. The reaction can be conducted smoothly at a temperature ranging from room temperature to 200° C, preferably 100° - 150° C.

The products obtainable from the first stage of the reaction are principally α-acyloxysulfide derivatives having the formula (VII')

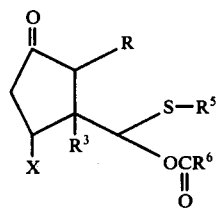

($R^3$, $R^5$, R and X are defined above; and $R^6$ is the alkyl, aralkyl or aryl group of the organic acid anhydride used).

In the second stage of the reaction, the products which may or may not be separated, are then hydrolyzed to complete Step VII. The hydrolysis can be conducted in the presence of either an acid or an alkali.

The presence of a catalytic amount of the acid or the alkali is sufficient for the completion of the hydrolysis.

Suitable acid catalysts include mineral acids such as hydrochloric acid, sulfuric acid and, perchloric acid; and organic acids such as p-toluenesulfonic acid, trifluoromethanesulfonic acid and the like.

Suitable alkali catalysts include alkali metal hydroxides such as sodium hydroxide, potassium hydroxide, and alkali metal alkoxides such as sodium methoxide, sodium ethoxide, potassium-t-butoxide and the like.

The second stage of the reaction should be conducted in an aqueous medium.

However, in order to increase the solubility of the compounds having the formula (VII'), it is preferred to use a polar solvent such as an alcohol, e.g., methanol, ethanol and, t-butanol; ethers, e.g., ethyl ether, tetrahydrofuran and, dimethoxyethane; acetonitrile, dimethylformamide, dimethyl sulfoxide and the like, as a cosolvent for hydrolysis. The second stage reaction can be conducted smoothly at a temperature ranging from room temperature to 150° C, preferably 50° - 100° C. The required reaction time is usually 30 minutes to 3 hours. It is also possible to obtain the object compound, i.e., the 3-formylcyclopentanone derivative (VIII) more selectively and in a purer state, by adding mercuric chloride or mercuric oxide to the reaction system. These mercury salts usually act as scavengers of organic sulfur compounds which are formed as by-products during the hydrolysis.

Reference 1

In accordance with the method disclosed by L. Weiler [J. Amer, Chem. Soc., 96, 1082 (1974)] sodium hydride (480 mg; 20 m mol) was suspended in 50 ml of the tetrahydrofuran (THF) under argon atmosphere.

The suspension was cooled to 0° C and a solution of methyl acetoacetate (2.32 g; 20 m mol) in 5 ml of THF was added to it with stirring. After 10 minutes, a solution of n-butyl lithium (20 m mol) in n-hexane was added dropwise to the mixture.

After 15 minutes from the addition, a solution of allyl bromide (2.40 g; 20 m mol) in 5 ml of THF was added to it.

The mixture was allowed to slowly warm to the room temperature and was stirred for 1 hour.

Then, the reaction mixture was treated by the conventional method and the residual oily material was distilled under a reduced pressure to obtain 1.95 g of 3-oxo-6-heptenoic acid methyl ester.

Yield: 63%;
Boiling point: 98° - 101° C/20 mmHg.

Reference 2

In accordance with the process of Reference 1, sodium hydride (1.20 g; 50 m mol), methyl acetoacetate (5.70 g; 50 m mol), n-butyl lithium (50 m mol) and trans-crotyl chloride (4.43 g; 50 m mol) were used to obtain 3.60 g of (E)-3-oxo-6-octenoic acid methyl ester.

Yield: 43%;
Boiling point: 110°-112° C/16 mmHg.

Reference 3

In accordance with the process of Reference 1, sodium hydride (550 mg; 23 m mol), methyl acetoacetate; (2.56 g; 22 m mol), n-butyl lithium (23 m mol) and 4-bromo-2-butyne were used to obtain 2.53 g of 3-oxo-6-octynoic acid methyl ester.

Yield: 76%;
Boiling point: 139° - 143° C/21 mmHg.

Reference 4

In methanol (20 ml), 3-oxo-6-octynoic acid methyl ester (2.09 g; 12.4 m mol) produced in Reference 3 was dissolved.

A Lindlar catalyst (200 mg) was added to the solution, and hydrogen (299 ml; 12.4 m mol) was absorbed with stirring at room temperature under normal pressure.

The reaction mixture was filtered through sellaite and the filtrate was condensed under a reduced pressure and the residue was distilled under a reduced pressure to obtain 1.54 g of (Z)-3-oxo-6-octenoic acid methyl ester.

Yield: 74%;
Boiling point: 113° - 114° C/15 mmHg.

Reference 5

In accordance with the method disclosed by S. B. Soloway [J. Amer, Chem. Soc. 69, 2677 (1974)], sodium hydride (20g; 0.83 mol) and dimethyl carbonate (75 g; 0.83 mol) were added to 110 ml of a dried ether and the mixture was vigorously stirred under refluxing.

A solution of allylacetone (40 g; 0.42 mol) in 110 ml of ether was added dropwise to the stirred mixture during about 5 hours. The mixture was allowed to stand overnight at room temperature, and was stirred for 1 hour under refluxing, and then 50 ml of acetic acid was added to the mixture to decompose the unreacted sodium hydride. The reaction mixture was treated by the conventional method and the remained oily material was distilled to obtain 50 g of 3-oxo-6-heptenoic acid methyl ester.

Yield: 89%;
Boiling point: 105° - 110° C/10 mmHg.

Reference 6

In accordance with the method disclosed by C. R. Hauser [J. Amer, Chem. Soc., 80, 6360 (1958)], a catalytic amount of the ferric chloride 6 hydrate and metallic potassium (11.7 g; 0.3 g atom) were dissolved in 450 ml of liquid ammonia.

After 30 minutes, a powdery complex compound produced by mixing acetylacetone (15 g; 10.15 mol) with ammonia was gradually added to the solution The mixture was stirred for about 1 hour, and then allyl bromide (18.2 g; 0.15 mol) was added to it. After stirring 1 hour, the solution was neutralized with solid ammonium chloride (15 g) and ammonia was removed by vaporiation. The reaction mixture was treated by the conventional method. The resulting oily product was distilled under a reduced pressure to obtain 10.1 g of 7-octene-2,4-dione.

Yield: 48%;
Boiling point: 74° – 76° C/14 mmHg.

Reference 7

In argon atmosphere, a 50% sodium hydride dispersion in mineral oil (960 mg; 20 m mol) was suspended to 50 ml of dried tetrahydrofuran. A solution of methyl acetoacetate (2.32 g; 20 m mol) in 5 ml of THF was added to said suspension with stirring.

After 10 minutes, a solution of n-butyl lithium (20 m mol) in n-hexane was added dropwise to the mixture.

After the addition, the mixture was further stirred at the temperature (about 0° C) for 30 minutes. The reaction mixture was cooled to −40 ° C, and then a solution of acrolein (1.12 g; 20 m mol) in 5 ml of THF was added dropwise to the reaction mixture. After the addition, the mixture was further stirred at the temperature for about 4 hours. The mixture was gradually warmed to the room temperature and most of the solvent was distilled under a reduced pressure. The concentrated reaction mixture was treated with a diluted hydrochloric acid and then with ether. The aqueous layer was extracted with ether.

The ether solution was washed with a saturated aqueous solution of sodium chloride and dried over anhydrous magnesium sulfate. The solution was filtered and then the solvent was distilled off under a reduced pressure. The residue was distilled under a reduced pressure to obtain 2.25 g of 5-hydroxy-3-oxo-6-heptenoic acid methyl ester.

Yield: 65%;
Boiling point: 105° – 107° C/1.0 mmHg;
Infrared spectrum (cm$^{-1}$); 1745, 1715, 1645;
Nuclear magnetic resonance (NMR) spectrum (CCl$_4$)$\delta$:

2.66 (ABX, J$_{AX}$ = 6.5, J$_{BX}$ = 5.5 Hz, 2H), 3.33 (broad s, 1H)

3.43 (s. 2H), 3.68 (s, 3H), 4.48 (m, 1H), 4.94 – 5.35 (m, 2H), 5.64 – 6.02 (m, 1H).

Reference 8

To a solution of 5-hydroxy-3-oxo-6-heptenoic acid methyl ester (2.18 g; 12.7 m mol) in 50 ml of dried ether, was added dihydropyran (2.18 g; 12.7 m mol) and a catalytic amount of p-toluenesulfonic acid with stirring and cooling in a water bath.

The mixture was stirred overnight at the room temperature. An aqueous solution of sodium bicaronate was added to the reaction mixture and the product was extracted with ether and was treated by the conventional method to obtain viscous oily product. The product was purified by a silica gel column chromatography (ethyl acetate: n-hexane = 1.5 : 8.5) to obtain 2.7 g of 3-oxo-5-(2'-tetrahydropyranyloxy)-6-heptenoic acid methyl ester as oil.

Yield: 76%;
Infrared spectrum (cm$^{-1}$): 1750, 1720, 1655, 1625, 1020,
NMR spectrum (CCl$_4$)$\delta$:
1.24 – 1.98 (m, 6H), 2.21 – 3.02 (m, 2H), 3.20 – 3.98 (m, 2H), 3.43 (s, 2H), 3.70 (s, 3H), 4.38 – 4.75 (m, 2H), 4.87 – 6.20 (m, 3H).

Reference 9

In accordance with the process of Reference 1, the dianion solution of methyl acetoacetate (20 m mol) was produced. The solution was cooled to −40° C. A solution of acrolein (1.12 g; 20 m mol) in 5 ml of THF was added to the solution with stirring. The mixture was stirred at −40° C for 30 minutes and was warmed to 0° C during 1 hour and then was cooled to −40° C again.

To the mixture was added with stirring a solution of benzyl bromide (3.08 g ; 18 m mol) in 6 ml of a mixture of THF : HMPA = 1 : 1 and the resulting mixture was kept at −10° C overnight.

The reaction mixture was treated by the conventional method and the oily product was purified by a silica gel column chromatography with a solvent of ethyl acetate and n-hexane (1 : 9) to obtain 1.1 g of 5-benzyloxy-3-oxo-6-heptenoic acid methyl ester.

Yield: 23% based on benzyl bromide:
Infrared spectrum (cm$^{-1}$): 1750, 1720, 1655, 1630;
NMR spectrum (CCl$_4$)$\delta$:
2.13 – 3.17 (m, 2H), 3.31 (s, 2H), 3.63 (s, 3H), 3.93 – 4.67 (m, 3H), 4.97 – 6.06 (m, 3H), 6.93 – 7.44 (m, 5H).

Reference 10

To an ice-cooled solution of 5-hydroxy-3-oxo-6-heptanoic acid methyl ester (344 mg, 2 m mol) of Reference 7 and trimethylsilyl chloride (217 mg; 2 m mol) in 25 ml of dried ether was added dropwise a solution of triethylamine (202 mg, 2 m mol) in 3 ml of dried ether.

The mixture was stirred overnight at the room temperature and was poured into a saturated aqueous solution of sodium chloride and the product was extracted with ether.

The ether extract was dried over anhydrous magnesium sulfate. After filtering, the solvent was distilled off under a reduced pressure and the residue was purified by a silica gel column chromatography to obtain 360 mg of 3-oxo-5-trimethyloxy-6-heptenoic acid methyl ester as an oily product.

Yield: 74%;
Infrared spectrum (cm$^{-1}$); 1750, 1720, 1650, 1630;
NMR spectrum (CCl$_4$)$\delta$:
0.07 (s, 9H), 2.10 – 3.00 (m, 2H), 3.33 (s, 2H), 3.69 (s, 3H), 4.32 – 4.77 (m, 1H), 4.86 – 6.10 (m, 3H).

EXAMPLE 1

A solution of p-toluenesulfonyl azide (592 mg; 3 m mol) in 1 ml of acetonitrile was added at room temperature to a solution of 3-oxo-6-heptenoic acid methyl ester (468 mg; 3 m mol) and triethylamine (306 mg; 3 m mol) in 5 ml of acetonitrile.

The mixture was stirred for about 2 hours and the solvent was distilled off under a reduced pressure and the product was dissolved in with 50 ml of ether.

The solution was washed with 5% aqueous solution of potassium hydroxide until no color of the aqueous phase was found and was further washed with a saturated aqueous solution of sodium chloride.

The ether solution was dried over anhydrous magnesium sulfate and was filtered and condensed under a reduced pressure to obtain 530 mg of 2-diazo-3-oxo-6-heptenoic acid methyl ester as yellow oily product. The crude product can be purified by the distillation under a reduced pressure.

Yield: 97%;
Boiling point: 67° – 68° C/0.4 mmHg;
Infrared spectrum (cm$^{-1}$); 2120, 1725, 1655;
NMR spectrum (CCl$_4$)δ:
3.77 (s, 3H), 4.65 – 5.20 (m, 2H), 5.47 – 6.13 (m, 1H)

EXAMPLE 2

In accordance with the process of Example 1, 7-octene-2,4-dione (8.4 g; 60 m mol), triethylamine (6.1 g; 60 m mol) and p-toluenesulfonyl azide (11.8 g; 60 m mol) were used as the starting materials and the final product was purified by a silica gel column chromatography with a mixture of ethylacetate: n-hexane = 1 : 9, to obtain 8.4 g of 7-octene-3-diazo-2,4-dione as yellow oily product.

Yield: 84%;
Infrared spectrum (cm$^{-1}$); 2115, 1665;
NMR spectrum (CCl$_4$)δ:
2.10 – 2.50 (m, 2H), 2.30 (s, 3H), 2.50 – 2.90 (m, 2H), 4.63 – 5.20 (m, 2H), 5.37 – 6.16 (m, 1H).

EXAMPLE 3

In accordance with the process of Example 2, (Z)-3-oxo-6-octenoic acid methyl ester (0.77 g; 4.52 m mol), triethylamine (0.46 g; 4.52 m mol), p-toluenesulfonylazide (0.89 g; 4.52 m mol) were used as starting materials to obtain 0.77 g of (Z)-2-diazo-3-oxo-6-octenoic acid methyl ester as yellow oily product.

Yield: 87%;
Infrared spectrum (cm$^{-1}$); 2130, 1730, 1655;
NMR spectrum (CCl$_4$)δ:
1.65 (d, J = 4 Hz, 3H), 2.03 – 3.13 (m, 4H), 3.83 (s, 3H), 5.03 – 5.70 (m, 2H).

EXAMPLE 4

In accordance with the process of Example 2, (E)-3-oxo-6-octenoic acid methyl ester (3.42 g; 20.1 m mol), triethylamine (2.03 g; 20.1 m mol), p-toluenesulfonyl azide (3.99 g; 20 m mol) were used as starting materials to obtain 3.37 g of (E)-2-diazo-3-oxo-6-octenoic acid methyl ester as yellow oily product.

Yield: 86%;
Infrared spectrum (cm$^{-1}$); 2140, 1750, 1660, 966;
NMR spectrum (CCl$_4$)δ:
1.63 (d, J = 6 Hz, 3H), 1.85 – 3.33 (m, 4H), 3.80 (s, 3H), 5.20 – 5.57 (m, 2H).

EXAMPLE 5

In accordance with the process of Example 1, 3-oxo-7-methyl-6-octenoic acid methyl ester (0.54 g; 2.93 m mol), triethylamine (0.30 g; 2.93 m mol) and p-toluenesulfonyl azide (0.61 g; 2.93 m mol) were used as starting materials to obtain 0.55 g of 2-diazo-3-oxo-7-methyl-6-octenoic acid methyl ester as yellow oily product.

The crude product was purified by distillation under a reduced pressure.

Yield: 90%;
Boiling point: 86° – 92° C/0.15 mmHg;
Infrared spectrum (cm$^{-1}$): 2130, 1725, 1660;
NMR spectrum (CCl$_4$) : 1.37 – 1.80 (broad d, J=2Hz, 6H), 1.90 – 2.57 (m, 2H), 2.57 – 3.07 (m, 2H), 3.82 (s, 3H), 4.85 – 5.32 (broad t, J= 7Hz, 1H).

EXAMPLE 6

In accordance with the process of Example 2, 3-oxo-5-(2'-tetrahydropyranyloxy)-6-heptenoic acid methyl ester (1.84 g; 7.3 m mol), triethylamine (0.75 g; 7.5m mol) and p-toluenesulfonyl azide (1.46 g; 7.4 m mol) were used as starting materials to obtain 1.79 g of 2-diazo-3-oxo-5-(2'-tetrahydropyranyloxy)-6-heptenoic acid methyl ester as yellow viscous oily product.

Yield: 88%;
Infrared spectrum (cm$^{-1}$): 2125, 1725, 1655;
NMR spectrum (CCl$_4$)δ: 1.27 – 1.93 (m, 6H), 2.65 – 3.32 (m, 2H), 3.45 – 4.10 (m, 2H), 3.79 (s, 3H), 4.40 – 4.78 (m, 2H), 4.90 – 6.22 (m, 3H).

EXAMPLE 7

In accordance with the process of Example 2, 5-benzyloxy-3-oxo-6-heptenoic acid methyl ester (1.07 g; 4.1 m mol), p-toluenesulfonyl azide (810 mg; 4.1 m mol) and triethylamine (450 mg; 4.5 m mol) were used as starting materials to obtain 1.16 g of 5-benzyloxy-2-diazo-3-oxo-6-heptenoic acid methyl ester as yellow oily product.

Yield: 98%;
Infrared spectrum (cm$^{-1}$): 2125, 1725, 1655;
NMR spectrum (CCl$_4$)δ:
2.57 – 3.53 (m, 2H), 3.72 (s, 3H), 4.03 – 4.60 (m, 3H), 4.98 – 6.11 (m, 3H), 7.12 (broad s, 5H).

EXAMPLE 8

In accordance with the process of Example 2, 3-oxo-5-trimethylsilyloxy-6-heptenoic acid methyl ester (360 mg; 1.47 m mol), p-toluenesulfonyl azide(290 mg; 1.47 m mol) and triethylamine (150 mg; 147 m mol) were used as starting materials to obtain 330 mg of 2-diazo-3-oxo-5-trimethylsiloxy-6-heptenoic acid methyl ester as yellow oily product.

Yield: 83%;
Infrared spectrum (cm$^{-1}$): 2120, 1725, 1655;
NMR spectrum (CCl$_4$)δ: 0.07 (s, 9H), 2.90 (ABX, $J_{AB}$ = 16; $J_{AX}$= 8, $J_{BX}$= 5 Hz, 2H), 3.78 (s, 3H), 4.40 – 4.78 (m, 1H), 4.93 – 6.01 (m, 3H).

EXAMPLE 9

In argon atmosphere, the unpurified 2-diazo-3-oxo-6-heptenoic acid methyl ester of Example 1 (4.55 g; 25 m mol) was dissolved in 100 ml of benzene.

An anhydrous cupric sulfate (2.5 g) was added as a catalyst to the solution. The mixture was stirred for about 3 hours under refluxing.

After confirming the disappearance of the starting materials by a thin layer chromatography, the reaction mixture was filtered through Celite column.

The solvent was distilled off from the filtrate under a reduced pressure and the remained oily product was distilled under a reduced pressure to obtain 2.92 g of 2-oxo-bicyclo [3.1.0] hexane-1-carboxylic acid methyl ester as oily product.

Yield: 69% based on methyl 3-oxo-6-heptenoate;
Boiling point: 90° C/0.7 mmHg;
NMR spectrum (CCl$_4$)δ: 1.33 (t, J = 5Hz, 1H), 1.77 – 2.30 (m, 4H), 2.30 – 2.73 (m, 2H), 3.68 (s, 3H);
Mass spectrum m/e (%): 154 (55), 126 (87), 123 (56), 113 (94), 67(62), 66 (54), 59(75);

Infrared spectrum (cm$^{-1}$): 1755, 1725.

EXAMPLE 10

In accordance with the process of Example 9, 7-octene-3-diazo-2,4-dione of Example 2 (8.17 g; 49 m mol) and anhydrous cupric sulfate (5 g) were used to obtain 2.52 g of 1-acetyl-2-oxo-bicyclo [3.1.0] hexane as oily product.

Yield: 37%;
Boiling point: 55° – 57° C/0.15 mmHg;
Infrared spectrum (cm$^{-1}$): 1725, 1690;
NMR spectrum (CCl$_4$)δ:1.37 (dd, J = 4 Hz, J= 6 Hz, 1H), 1.76 – 2.70 (m, 6H), 2.40 (s, 3H).

EXAMPLE 11

In accordance with the process of Example 9, (Z)-2-diazo-3-oxo-6-octenoic acid methyl ester of Example 3 (1.41 g; 7.2 m mol) and anhydrous cupric sulfate (1.41 g) were used as starting materials and the reaction product was purified by a silica gel column chromatography with a mixture of ethyl acetate and n-hexane (1 : 4) to obtain 0.66 g of endo-6-methyl-2-oxo-bicyclo [3.1.0] hexane-1-carboxylic acid methyl ester as oily product.

Yield: 55%;
Infrared spectrum (cm$^{-1}$): 1755, 1732;
NMR spectrum (CCl$_4$)δ: 1.14 (d, J = 6 Hz, 3H), 1.65 – 2.58 (m, 7H), 3.66 (s, 3H).

EXAMPLE 12

In accordance with the process of Example 9, (E)-2-diazo-3-oxo-6-octenoic acid methyl ester of Example 4 (3.33 g; 16.8 m mol) and anhydrous cupric sulfate (3.42 g) were used as starting materials to obtain 1.66 g of exo-6-methyl-2-oxo-bicyclo [3.1.0] hexane-1-carboxylic acid methyl ester as oily product.

Yield: 59%;
Boiling point: 97°–98° C/1.5 mmHg;
Infrared spectrum (cm$^{-1}$): 1755, 1730;
NMR spectrum (CCl$_4$)δ: 1.19 (d, J = 6 Hz, 3H), 1.46 – 2.58 (m, 6H), 3.65 (s, 3H).

EXAMPLE 13

In 30 ml of anhydrous xylene, 2-diazo-3-oxo-5-(2'-tetrahydropyranyloxy)-6-heptenoic acid methyl ester (1.05 g: 3.8 m mol) was dissolved.

A copper acetylacetone complex (100 mg) was added to the solution and the mixture was heated for 3 hours under refluxing.

After distilling off most of xylene under a reduced pressure, 30 ml of ether was added to the residue.

The precipitate formed was filtered and the filtrate was condensed under a reduced pressure. The residue was purified by a silica gel column chromatography with a mixture of ethyl acetate and n-hexane (3 : 7) to obtain 500 mg of two types of isomers of 2-oxo-4-(2'-tetrahydropyranyloxy)-bicyclo [3.1.0] hexane-1-carboxylic acid methyl ester as viscous oily product.

Yield: 52%;
Isomer obtained from the first fraction.
Infrared spectrum (cm$^{-1}$): 1765, 1740;
NMR spectrum (CCl$_4$)δ: 1.15 – 3.08 (m, 11H), 3.21 – 3.98 (m, 2H), 3.67 (s, 3H), 4.41 – 4.92 (m, 2H);
Isomer obtained from the latter fraction.
Infrared spectrum (cm$^{-1}$); 1765, 1740;
NMR spectrum (CCl$_4$)δ: 1.10 – 3.12 (m, 10H), 1.29 (t, J = 5 Hz, 1H), 3.21 – 4.13 (m, 2H), 3.69 (s, 3H), 4.14 – 4.40 (m, 1H), 4.63 – 4.92 (m, 1H).

EXAMPLE 14

In accordance with the process of Example 13, 5-benzyloxy-2-diazo-3-oxo-6-heptenoic acid methyl ester (1.16 g; 4 m mol) and copper acetylacetone complex (100 mg) were dissolved in 30 ml of anhydrous xylene.

The reaction product was purified by a silica gel column chromatography to obtain two types of isomers of 4-benzyloxy-2-oxo-bicyclo [3.1.0] hexane-1-carboxylic acid methyl ester (248 mg) as oily product.

Yield: 25%
Isomer obtained from the first fraction.
Infrared spectrum (cm$^{-1}$): 1765, 1745;
NMR spectrum (CCl$_4$)δ:
1.61 (t, J = 5 Hz), 1.65 – 2.90 (m, 4H), 3.67 (s, 3H), 4.10 – 4.52 (m, 1H), 4.50 (s, 2H), 7.22 (broad s, 5H),
Isomer obtained from the latter fraction.
Infrared spectrum (cm$^{-1}$): 1765, 1740;
NMR spectrum (CCl$_4$)δ: 1.10 (t, J = 5 Hz), 1.67 – 2.86 (m, 4H), 3.73 (s, 3H), 3.92 – 4.25 (m, 1H), 4.53 (s, 2H), 7.24 (broad s, 5H).

EXAMPLE 15

In accordance with the process of Example 13, 2-diazo-3-oxo-5-trimethylsilyloxy-6-heptenoic acid methyl ester (2.63 g; 9.7 m mol) and copper acetylacetone complex (200 mg) were dissolved in 20 ml of anhydrous benzene. The reaction product was purified by a silica gel column chromatography to obtain two types of isomers of 2-oxo-4-trimethylsiloxy-bicyclo [3.1.0] hexane-1-carboxylic acid methyl ester (1.05 g).

Yield: 45%;
Infrared spectrum (cm$^{-1}$): 1765, 1745.

EXAMPLE 16

Thiophenol (660 mg; 6 m mol) was added to a solution of potassium t-butoxide (650 mg; 6 m mol) in 5 ml of t-butyl alcohol. The mixture was stirred for 10 minutes.

A solution of 2-oxo-bicyclo[3.1.0] hexane-1-carboxylic acid methyl ester of Example 9 (924 mg, 6 m mol) in 2 ml of t-butyl alcohol was added to the mixture. After stirring the mixture at the room temperature for about 30 minutes, most of the solvent was distilled off under a reduced pressure.

Ether was added to the residue and a dilute hydrochloric acid was added to acidity the solution, and the ethereal solution was washed with a saturated aqueous solution of sodium chloride and was dried over anhydrous magnesium sulfate and was filtered. The solvent was distilled off under a reduced pressure. The remained crystals were recrystallized from ether and n-hexane to obtain 2-oxo-5-phenylthiomethylcyclopentanecarboxylic acid methyl ester as white crystals.

Yield: 93%;
Melting point: 41° – 42° C;
Infrared spectrum (cm$^{-1}$); 1765, 1730, 1585, 1570, 1480, 1440, 1223, 1024, 740, 690;
NMR spectrum (CCl$_4$) δ:
1.37 – 2.67 (m, 5H), 2.70 – 3.50 (m, 3H), 3.68 (s, 3H), 7.03 – 7.65 (m, 5H);
Mass spectrum m/e (%)
264(18), 141(65), 123 (65), 110(30), 109(100).

EXAMPLE 17

In accordance with the process of Example 16, potassium t-butoxide (336 mg; 3 m mol), benzyl mercaptan (372 mg; 3 m mol) and 2-oxo-bicyclo [3.1.0] hexane-1- carboxylic acid methyl ester (463 mg; 3 m mol) were used in the reaction, and the reaction product was purified by a silica gel column chromatography with ethyl acetate and n-hexane (1.5; 8.5) to obtain 650 mg of 5-benzylthiomethyl-2-oxo-cyclopentanecarboxylic acid methyl ester as an oil.

Yield: 78%;
Infrared spectrum (cm$^{-1}$): 1760, 1730, 1660, 1620, 1600, 1495, 1130, 770, 705;
NMR spectrum (CCl$_4$) δ: 0.97 – 2.70 (m, 6H), 2.82 (m, 2H), 3.63 (m, 5H), 7.12 (m, 5H).

EXAMPLE 18

In accordance with the process of Example 17, potassium t-butoxide, (336 mg; 3 m mol), n-hexyl mercaptan (354 mg; 3 m mol) and 2-oxo-bicyclo[3.1.0]hexane-1-carboxylic acid methyl ester (463 mg; 3 m mol) were used to obtain 500 mg of 5-hexylthiomethyl-2-oxo-cyclopentanecarboxylic acid methyl ester.

Yield: 61%;
Infrared spectrum (cm$^{-1}$): 1760, 1730, 1660, 1620;
NMR spectrum (CCl$_4$) δ: 1.90 (t, J = 6.5 Hz, 3H), 1.08 – 3.12 (m, 18H), 3.71 (s, 3H).

EXAMPLE 19

In accordance with the process of Example 17, potassium t-butoxide (0.44 g; 3.9 m mol), thiophenol (0.43 g; 3.9 m mol) and endo-6-methyl-2-oxo-bicyclo[3.1.0]hexane-1-carboxylic acid methyl ester (0.66 g; 3.9 m mol) were used to obtain 0.76 g of one of isomers of 2-oxo-5-(1'-phenylthioethyl)-cyclopentanecarboxylic acid methyl ester as an oil.

Yield: 69%
Infrared spectrum (cm$^{-1}$): 1760, 1730, 1655, 1620.

EXAMPLE 20

In accordance with the process of Example 16, potassium t-butoxide (560 mg; 5 m mol), thiophenol (550 mg; 5 m mol) and exo-6-methyl-2-oxo-bicyclo[3.1.0]hexane-1-carboxylic acid methyl ester (840 mg; 5 m mol) were used to obtain 1.14 g of one of isomers of 2-oxo-5-(1'-phenylthioethyl)-cyclopentanecarboxylic acid methyl ester as white crystals. This isomer showed completely different spectra compared with the isomer of Example 19.

Yield: 82%;
Melting point: 57° – 58° C;
Infrared spectrum (cm$^{-1}$): 1750, 1720.

EXAMPLE 21

In accordance with the process of Example 17, potassium t-butoxide (246 mg; 2.2 m mol), thiophenol (220 mg, 2 m mol) and 2-oxo-4-trimethylsiloxy-bicyclo[3.1.0]hexane-1-carboxylic acid methyl ester (484 mg; 2 m mol) were used to obtain 470 mg of 2-oxo-5-phenylthiomethyl-4-trimethylsiloxy-cyclopentanecarboxylic acid methyl ester as a viscous oil.

Yield: 67%;
Infrared spectrum (cm$^{-1}$): 1765, 1730, 1665, 1620.

EXAMPLE 22

In 20 ml of acetone, benzyl bromide (200 mg; 1.2 m mol) and 2-oxo-5-phenylthiomethyl-cyclopentanecarboxylic acid methyl ester of Example 16 (264 mg; 1 m mol) were dissolved.

Potassium carbonate (280 mg; 2 m mol) was added to said solution and the mixture was stirred for 7 hours under refluxing.

The reaction mixture was cooled to the room temperature and the precipitate was filtered off and the solvent was distilled off under a reduced pressure. The residue was purified by a silica gel column chromatography with ethyl acetate and n-hexane (1.5 : 8.5) to obtain 330 mg of 1-benzyl-2-oxo-5-phenylthiomethyl-cyclopentanecarboxylic acid methyl ester as an oil.

Yield: 93%;
Infrared spectrum (cm$^{-1}$): 1745, 1725, 1605, 1587, 1500, 1202, 750, 710;
NMR spectrum (CCl$_4$) δ: 1.40 – 2.52 (m, 5H), 2.53 – 3.52 (m, 4H), 3.67 (s, 3H), 6.57 – 7.48 (m, 10H).

EXAMPLE 23

In accordance with the process of Example 22, 2-oxo-5-phenylthiomethylcyclopentanoic acid methyl ester (792 mg; 3 m mol), ethyl bromoacetate (501 mg; 3 m mol) and potassium carbonate (415 mg; 3 m mol) were used to obtain 674 mg of 1-ethoxycarbonylmethyl-2-oxo-5-phenylthiomethyl-cyclopentanecarboxylic acid methyl ester as a viscous oil.

Yield: 64%;
Infrared spectrum (cm$^{-1}$): 1755, 1730;
NMR spectrum (CCl$_4$) δ: 1.13 (t, J = 6 Hz, 3H), 1.52 – 3.34 (m, 9H), 3.63 (s, 3H), 3.90 (q, J = 6 Hz, 3H), 6.97 – 7.33 (m, 5H).

EXAMPLE 24

In 10 ml of anhydrous methanol, potassium t-butoxide (561 mg; 5 m mol) was dissolved.

A solution 2-oxo-5-phenylthiomethyl-cyclopentanecarboxylic acid methyl ester (1.32 g; 5 m mol) in 3 ml of methanol was added dropwise to said solution cooled with ice water, with stirring.

After 30 minutes the solvent was completely distilled off under a reduced pressure to obtain white potassium salt of 2-oxo-5-phenylthiomethylcyclopentanecarboxylic acid methyl ester. The product was dissolved in 20 ml of anhydrous toluene. A solution of 7-iodoheptanoic acid methyl ester (1.35 g; 5 m mol) in 3 ml of toluene was added to said solution. The reaction product was gradually with stirring and was heated for 24 hours under refluxing. The reaction mixture was cooled to the room temperature and then 30 ml of ether and a dilute hydrochloric acid were added to it. The ether phase was separated and washed with a saturated aqueous solution of sodium chloride and was dried over anhydrous magnesium sulfate.

The solution was filtered and the solvent was distilled off under a reduced pressure to afford a viscous oil. The product was purified by a silica gel column chromatography with ethyl acetate and n-hexane (2 : 8) to obtain 1.3 g of 1-(6'-methoxycarbonylhexyl)-2-oxo-5-phenylthiomethyl-cyclopentacarboxylic acid methyl ester as an oil.

Yield: 64%;
Infrared spectrum (cm$^{-1}$): 1735, 1190, 735, 690;
NMR spectrum (CCl$_4$) δ: 0.93 – 1.98 (m, 13H), 2.0 – 2.5 (m, 4H), 2.97 (m, 2H), 3.30 (s, 6H), 7.02 – 7.43 (m, 5H).

EXAMPLE 25

In 20 ml of dimethylformamide, 1-benzyl-2-oxo-5-phenylthiomethylcyclopentanecarboxylic acid methyl ester of Example 22 (2.55 g; 7.2 m mol) was dissolved, and then lithium iodide (965 mg; 7.2 m mol) was added to said solution.

The mixture was vigorously stirred in argon atmosphere under refluxing. After 3 hours, the reaction mixture was cooled to the room temperature and 30 ml of ether was added and then an aqueous solution of ammonium chloride was added to the reaction mixture.

The ether phase was separated and was washed with a saturated aqueous solution of sodium chloride, and was dried over anhydrous magnesium sulfate and the solution was filtered and the solvent was distilled off under a reduced pressure. The residue was purified by a silica gel column chromatography with ethyl acetate and n-hexane (1 : 9) to obtain 1.79 g of 2-benzyl-3-phenylthiomethyl-cyclopentanone as an oil.

Yield: 84%;

Infrared spectrum (cm$^{-1}$): 1740, 1600, 1580, 1495, 745, 705, 695.

NMR spectrum (CCl$_4$) δ: 1.13–2.50(m, 5H), 2.50–3.30 (m, 5H), 6.75–7.52 (m, 5H).

EXAMPLE 26

In accordance with the process of Example 25, 1-ethoxycarbonylmethyl-2-oxo-5-phenylthiomethyl-cyclopentanecarboxylic acid methyl ester (640 mg; 1.83 m mol) and lithium iodide (250 mg; 1.85 m mol) were used to obtain 420 mg of 2-ethoxycarbonylmethyl-3-phenylthiomethyl-cyclopentanone as an oil.

Yield: 78%;

Infrared spectrum (cm$^{-1}$): 1740, 1185;

NMR spectrum (CCl$_4$) δ: 1.18 (t, J = 6 Hz, 3H), 1.92 – 2.42 (m, 6H), 2.52 (m, 2H), 2.99 (ABX, $J_{AB}$ = 13, $J_{AX}$ = 8, $J_{BX}$ = 5 Hz, 2H), 3.99 (q, J = 7 Hz, 2H), 6.95 – 7.34 (m, 5H).

EXAMPLE 27

The unpurified viscous oily product of Example 24 (1.57 g) which is mainly 1-(6'-methoxycarbonylhexyl)-2-oxo-5-phenylthiomethyl-cyclopentanecarboxylic acid methyl ester was dissolved in 20 ml of dimethylformamide, and lithium iodide (670 mg; 5 m mol) was added to said solution and the mixture ws stirred for 3 hours under refluxing.

The reaction mixture was cooled to the room temperature and then 50 ml of ether and an aqueous solution of sodium chloride were added to it. The ether phase was separated and was washed with a saturated aqueous solution of sodium chloride and dried over anhydrous magnesium sulfate.

The solution was filtered and was concentrated under a reduced pressure. The residue was purified by a silica gel column chromatography with ethyl acetate and n-hexane (1 : 9) to obtain 942 mg of 2-oxo-5-phenylthiomethyl-cyclopentaneheptanoic acid methyl ester as an oil.

Yield: 55%, based on 2-oxo-5-phenylthiomethyl-cyclopentanecarboxylic acid methyl ester;

Infrared spectrum (cm$^{-1}$): 1740, 1585, 1570, 1485, 1440, 1165, 740, 690;

NMR spectrum (CCl$_4$) δ: 1.05 – 1.80 (m, 13H), 1.90 – 2.38 (m, 5H), 2.80 (dd, J = 13 Hz, J = 7 Hz, 1H), 3.17 (dd, J = 13 Hz, J = 4 Hz, 1H), 3.54 (s, 3H), 7.02 – 7.38 (m, 5H).

EXAMPLE 28

The 1-benzyl-2-oxo-5-phenylthiomethyl-cyclopentanecarboxylic acid methyl ester of Example 22 (354 mg; 1 m mol) was added to 20 ml of a mixture of conc. sulfuric acid and water (1 : 3) and the mixture was vigorously stirred for 5 hours under refluxing. After cooling it to the room temperature, 30 ml of ether was added and then an aqueous solution of ammonium chloride was added to the reaction mixture. The ether phase was separated and was washed with a saturated aqueous solution of sodium chloride and was dried over anhydrous magnesium sulfate. The solution was filtered and the solvent was distilled off under a reduced pressure.

The residue was purified by a silica gel column chromatography with ethyl acetate and n-hexane (1 : 9) to obtain 250 mg of 2-benzyl-3-phenylthiomethyl-cyclopentanone as an oil.

Yield: 84%

EXAMPLE 29

The 2-benzyl-3-phenylthiomethyl-cyclopentanone of Example 25 (1.41 g; 4.75 m mol) was dissolved in 50 ml of methylene chloride, and then m-chloroperbenzoic acid having a purity of 85% (970 mg; 4.75 m mol) was added and the mixture was stirred at the room temperature for 3 hours.

After confirming the disappearance of the starting material by a thin layer chromatography, ammonia gas was introduced into the reaction mixture to precipitate ammonium m-chlorobenzoate.

The precipitate was filtered through Celite column. The methylene chloride phase was separated and washed with an aqueous solution of sodium thiosulfate and then water and was dried over anhydrous magnesium sulfate. The solution was filtered and condensed under a reduced pressure.

The residue was purified by a silica gel column chromatography with methylene chloride and ethanol (19 : 1) to obtain 1.22 g of 3-benzenesulfinylmethyl-2-benzyl-cyclopentanone as a viscous oil.

Yield: 84%;

Infrared spectrum (cm$^{-1}$); 1740, 1602, 1583, 1043, 755, 700;

NMR spectrum (CCl$_4$) δ: 1.30 –2.4 (m, 6H), 2.4 – 3.43 (m, 4H), 6.90 – 7.38 (m, 5H), 7.47 (s, 5H).

EXAMPLE 30

In accordance with the process of Example 29, 2-oxo-5-phenylthiomethyl-cyclopentaneheptanoic acid methyl ester of Example 27 (890 mg; 2.58 m mol) and m-chloroperbenzoic acid having a purity of 85% (5.25 mg; 2.58 m mol) were used to obtain 800 mg of 5-benzenesulfinylmethyl-2-oxo-cyclopentaneheptanoic acid methyl ester as viscous oil.

Yield: 85%;

Infrared spectrum (cm$^{-1}$); 1740, 1165, 1040, 750, 690;

NMR spectrum (CCl$_4$) δ: 0.82 – 2.7 (m, 18H), 2.9 (m, 2H), 3.61 (s, 3H), 7.27 – 7.73 (m, 5H).

EXAMPLE 31

The 3-benzenesulfinylmethyl-2-benzyl-cyclopentanone of Example 29 (420 mg; 1.35 m mol) was dissolved in 10 ml of acetic anhydride and then sodium acetate (110 mg; 1.35 m mol) was added to it. The mixture was vigorously stirred for 5 hours under refluxing. After cooling the reaction mixture to the room temperature and most of the solvent was distilled off under a reduced pressure. The residue was admixed with 30 ml of benzene to dissolve the organic products and precipitate was filtered.

The solvent was distilled off from the filtrate to obtain α-acetoxysulfide derivatives.

The oily products was mixed with 40 ml of a mixture of methanol and water (1 : 1) and then 0.5 ml of conc.

sulfuric acid and mercuric chloride (735 mg; 2.70 m mol) were added to it. The mixture was vigorously stirred for 30 minutes under refluxing. After cooling the reaction mixture, the precipitate was filtered through Celite column and the filtrate was condensed under a reduced pressure to remove most of methanol.

The residue was mixed with 50 ml of ether and the ether layer was separated and washed with a saturated aqueous solution of ammonium chloride and was dried over anhydrous magnesium sulfate. The solution was filtered and the solvent was distilled off under a reduced pressure.

The residue was purified by a silica gel column chromatography with ethyl acetate and n-hexane (3 : 17) to obtain 150 mg of 2-benzyl-3-formylcyclopentanone (55%) and dimethylacetal thereof (120 mg; 36%). The latter can be quantitatirely converted to the former by refluxing it in a mixture of acetone and water (9 : 1) which contained a catalylic amount of hydrochloric acid.

Yield: 91%;

Infrared spectrum (cm$^{-1}$); 2810, 2710, 1740, 1725, 760, 740, 720;

NMR spectrum (CCl$_4$)δ: 1.63 - 2.52 (m, 4H), 2.53 - 3.44 (m, 4H), 6.90 - 7.42 (m, 5H), 9.43 (d, J = 2 Hz, 1H);

Mass spectrum m/e (%): 202(10), 173(100), 91(93).

EXAMPLE 32

The 5-benzenesulfinylmethyl-2-oxo-cyclopentaneheptanoic acid methyl ester of Example 30 (800 mg; 2.2 m mol) was dissolved in 10 ml of acetic anhydride, and sodium acetate (700 mg) was added to said solution. The mixture was vigorously stirred for 5 hours under refluxing.

After cooling it to the room temperature, most of the solvent was distilled off under a reduced pressure.

The residue was dissolved in 30 ml of benzene and the organic products were dissolved and the precipitate was filtered off. The solvent of the filtrate was distilled off under a reduced pressure to obtain α-acetoxy-sulfide derivatives as an oil.

The oily products were mixed with 40 ml of a mixture of methanol and water (1 : 1) and then 0.5 ml of conc. sulfuric acid and mercuric chloride (1.09 g; 4 m mol) were added to it. The mixture was vigorously stirred for 30 minutes under refluxing.

After cooling it to the room temperature, the product was treated in accordance with the process of Example 31 to obtain 250 mg of 5-formyl-2-oxo-cyclopentaneheptanoic acid methyl ester.

Yield: 45%;

Infrared spectrum (cm$^{-1}$): 2800, 2710, 1740, 1165;

NMR spectrum (CCl$_4$) δ: 0.94 - 2.95 (m, 18H), 3.61 (s, 3H), 9.65 (d, J = 2 Hz, 1H).

What is claimed as new and desired to be secured by Letters Patent is:

1. A process for producing a 3-formylcyclopentanone derivative having the formula

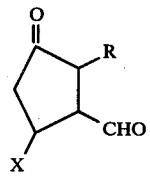

which comprises:

reacting a β-dicarbonyl compound having the formula

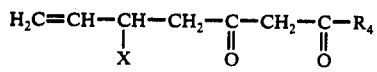

with an azide under basic conditions to produce an α-diazo-β-dicarbonyl compound having the formula

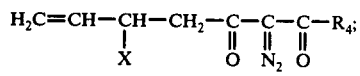

treating said product under conditions suitable for producing a carbene or carbenoid to produce a bicyclo hexane-2-one derivative having the formula:

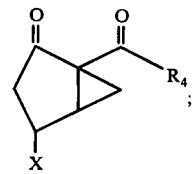

reacting said product with a mercaptan having the formula, R$_5$SH, in the presence of a base to produce a cyclopentanone derivative having the formula

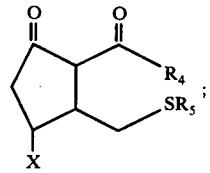

reacting said product with an alkylating agent having the formula RZ in the presence of a base to produce a cyclopentanone derivative having the formula

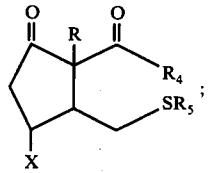

decarboxylating said product to produce a cyclopentane sulfide derivative having the formula

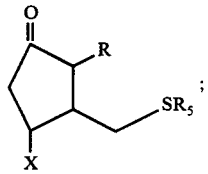

oxidizing said product to produce a cyclopentanone sulfoxide derivative having the formula

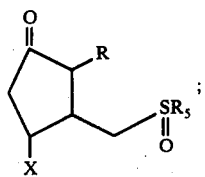

reacting said product with an acid anhydride; and treating the obtained product with an acid or a base; wherein $R_4$ is an alkyl or an alkoxy group; $R_5$ is a hydrocarbon group having less than 10 carbon atoms; R is a $C_{1-10}$ alkyl or $C_{2-10}$ alkenyl group substituted by a lower alkoxycarbonyl group; X is a hydrogen atom, an alkoxy group, a tetrahydropyranyloxy group or a silyloxy group; and Z is a leaving anion.

* * * * *